United States Patent
Abdel-Rahman et al.

(10) Patent No.: US 11,154,527 B2
(45) Date of Patent: *Oct. 26, 2021

(54) DERMATOPHYTOSIS PROPHYLAXIS AND TREATMENT

(71) Applicant: The Children's Mercy Hospital, Kansas City, MO (US)

(72) Inventors: Susan Abdel-Rahman, Kansas City, MO (US); Barry L. Preuett, Kansas City, MO (US); J. Steven Leeder, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/551,174

(22) Filed: Aug. 26, 2019

(65) Prior Publication Data

US 2019/0380990 A1 Dec. 19, 2019

Related U.S. Application Data

(63) Continuation of application No. 15/556,485, filed as application No. PCT/US2016/021406 on Mar. 8, 2016, now Pat. No. 10,406,132.

(60) Provisional application No. 62/130,427, filed on Mar. 9, 2015.

(51) Int. Cl.

| | |
|---|---|
| *A61K 31/22* | (2006.01) |
| *A61K 45/06* | (2006.01) |
| *A61K 31/366* | (2006.01) |
| *A61K 31/404* | (2006.01) |
| *A61K 31/4418* | (2006.01) |
| *A61K 31/47* | (2006.01) |
| *A61K 31/505* | (2006.01) |
| *A61K 36/00* | (2006.01) |
| *A61K 9/00* | (2006.01) |
| *A61K 31/40* | (2006.01) |
| *A61K 9/06* | (2006.01) |
| *A61K 47/10* | (2017.01) |

(52) U.S. Cl.
CPC ............ *A61K 31/22* (2013.01); *A61K 9/0014* (2013.01); *A61K 31/366* (2013.01); *A61K 31/40* (2013.01); *A61K 31/404* (2013.01); *A61K 31/4418* (2013.01); *A61K 31/47* (2013.01); *A61K 31/505* (2013.01); *A61K 36/00* (2013.01); *A61K 45/06* (2013.01); *A61K 9/06* (2013.01); *A61K 47/10* (2013.01)

(58) Field of Classification Search
CPC ...................................................... A61K 31/22
See application file for complete search history.

(56) References Cited

U.S. PATENT DOCUMENTS

| | | |
|---|---|---|
| 2003/0032578 A1 | 2/2003 | Jackson et al. |
| 2009/0258098 A1 | 10/2009 | Rolling et al. |
| 2011/0183944 A1 | 7/2011 | Ashton et al. |
| 2012/0164087 A1 | 6/2012 | Carter |
| 2012/0276182 A1 | 11/2012 | Baker, Jr. et al. |
| 2013/0116221 A1* | 5/2013 | Draijer .................. A23L 33/105 514/171 |

FOREIGN PATENT DOCUMENTS

WO 2009136214 11/2009

OTHER PUBLICATIONS

Search Report and Written Opinion in corresponding PCT Serial No. PCT/US2016/021406, dated May 17, 2016 (9 pages).
Office Action in corresponding U.S. Appl. No. 15/556,485, dated Apr. 9, 2018.
Office Action in corresponding U.S. Appl. No. 15/556,485, dated Oct. 26, 2018.
Bergman, et al., "Is there a role for statins in fungal infections?", Expert Rev. Anti Infect. Ther., vol. 11, issue 2, 2013, pp. 1391-1400.

* cited by examiner

Primary Examiner — Marcos L Sznaidman
(74) Attorney, Agent, or Firm — Hovey Williams LLP (57) ABSTRACT

A composition and method for the prophylaxis and treatment of topical fungal infections is provided. Generally, the composition includes an HMG-CoA reductase inhibitor and a carrier. In some forms, the composition further includes an anti-fungal agent. The method generally includes the steps of applying the composition topically once or multiple times. The composition and method can be used in combination with another form of fungal treatment, such as oral medications.

20 Claims, 2 Drawing Sheets

DERMATOPHYTOSIS PROPHYLAXIS AND TREATMENT

CROSS-REFERENCE TO RELATED APPLICATIONS

This application is a continuation of U.S. Ser. No. 15/556,485, filed Sep. 7, 2017, as the U.S. National Stage of International Patent Application No. PCT/US2016/021406, filed Mar. 8, 2016, which claims the priority benefit of U.S. Provisional Patent Application No. 62/130,427, filed Mar. 9, 2015, each of which is hereby incorporated by reference in its entirety.

FIELD OF INVENTION

The present disclosure is related to an HMG-CoA reductase (also referred to as a 'statin') composition for the prophylaxis and treatment of fungal infections of the hair and/or skin. More specifically, the present disclosure is related to a statin composition for the prophylaxis and treatment of fungal infections of the hair and/or scalp. A statin composition is provided for reducing the severity of a fungal infection, reducing the number of fungal cells, minimizing or eliminating spore shedding, decreasing the spread of fungal infections in a population, decreasing acquisition of fungal infections, decreasing susceptibility to fungal infections, decreasing the infection potential including preventing the spread of fungal infections to other children as well as further spreading on the same child, and preventing fungal infections or re-infections. The present disclosure also provides methods related to the treatment and prevention of fungal infections, specifically related to tinea capitis caused by *T. tonsurans*.

BACKGROUND OF THE INVENTION

Tinea capitis is a fungal infection of the scalp where dermatophytes in the *Trichophyton* and *Microsporum* genera invade the hair shaft and cause infection. Symptoms of tinea capitis generally present as a single or multiple patches of hair loss, sometimes with a "black dot" pattern that can be accompanied by additional symptoms such as inflammation, scaling, pustules, and itching. *Trichophyton tonsurans* (*T. tonsurans*) is one of the causes of tinea capitis, where this species of fungal infection is prevalent among school-aged children in the United States.

Tinea capitis is found to have become integrated into metropolitan communities having a striking presence and infection rate. Studies have shown that infection rates are higher than previously thought and two large scale studies of over 10,000 preschool and primary school-aged children showed schools had infection rates as high as 30%. (Abdel-Rahman, et al., Tracking *Trichophyton tonsurans* Through a Large Urban Child Care Center: Defining Infection Prevalence and Transmission Patterns by Molecular Strain Typing; Pediatrics, December 2006, Vol. 118, No. 6, pp. 2365-2373; Abdel-Rahman, et al.; The Prevalence of Infections With *Trichophyton tonsurans* in School children: the CAPITIS Study; Pediatrics; May, 2010; Vol. 125, No. 5, pp. 966-973). These studies also showed a large degree of genetic heterogeneity among the fungal isolates and a very low response rate to oral medicines administered for treatment. (Id.; Abdel-Rahman, et al., Tracking *Trichophyton tonsurans* Through a Large Urban Child Care Center: Defining Infection Prevalence and Transmission Patterns by Molecular Strain Typing; Pediatrics, December 2006, Vol. 118, No. 6, pp. 2365-2373; Abdel-Rahman et al., Griseofulvin has only a modest impact on eradicating carriage of *Trichophyton tonsurans*. Journal of Pediatric Pharmacology and Therapeutics, April 2009, Vol. 14, No. 2, pp. 94-99).

While oral medications for treating tinea capitis are known, these treatments face challenges. Often the infection is prevalent within a community of children, leading to vast opportunities for re-infection. Additionally, objects, such as bed sheets, pillows, hair brushes, stuffed toys, etc. carry the fungus and provide a means for re-infection. Objects in a classroom environment also have an impact on the prevalence of infection for the children in the classroom. Further, current oral medications used to treat tinea capitis have side effects such as liver toxicity and/or interactions with other drugs. This is in addition to the challenge presented when administering oral medication to a child, such as a child being unwilling to take a medication, ensuring enough of the medication was received, etc.

Several studies have investigated the antimycotic effect of statins, both alone and in combination with known antimycotic agents. As summarized in PCT/HU2009/000043 (the '043 application), no reference discussed therein found a generally valid antimycotic effect when using statins alone; no general synergistic antimycotic interaction between statins and known antimycotic agents can be detected; the presence or absence of a synergistic effect of statins and known antimycotic agents was different from species to species; and the fact that a combination of a statin and an antimycotic agent showed some synergistic effect does not mean that the effect could be achieved using clinically acceptable dosage ranges. The '043 application showed an additive effect for most combinations of fluvastatin and ketoconazole in *Candida albicans*, an additive effect for most combinations of pravastatin and miconazole in *Candida glabrata*, an additive effect for most combinations of simvastatin and primycin in *Candida glabrata*, a synergistic effect for most combinations of atorvastatin and itraconazole in *Aspergillus fumigatus*, an additive effect for most combinations of fluvastatin and miconazole in *Aspergillus flavus*, and a synergistic effect for most combinations of atorvastatin and ketoconazole in *Rhizopus oryzae*. However, in addition to the summary of the antimycotic effect of statins provided in the '043 application, it can be appreciated that the organisms studied in the '043 application are not dermatophytes.

SUMMARY OF THE INVENTION

The present disclosure overcomes the problems present in the prior art and provides a topical composition incorporating a statin for preventing and treating fungus. The topical composition of the present disclosure generally comprises an amount of an agent and an amount of a vehicle or carrier suited for topical administration. The topical composition of the present disclosure is effective for at least one of the prophylaxis and/or treatment of a topical fungal infection, reducing the number of fungal cells, minimizing or eliminating spore shedding, decreasing the spread of fungal infections, decreasing acquisition of fungal infections, decreasing susceptibility to fungal infections, decreasing the infection potential including preventing the spread of fungal infections to other children as well as further spreading on the same child, preventing fungal infections or re-infections, and combinations thereof. In terms of a population of individuals, the topical composition described herein is effective at reducing the incidence of fungal infections, decreasing acquisition of fungal infections, decreasing susceptibility to fungal infections, decreasing the infection potential including preventing the spread of fungal infections to other children as well as further spreading on previously infected children, preventing fungal infections or re-infections, and combinations thereof, in the population. The topical composition of the present disclosure is generally applied to a topical fungal infection or applied to an area where topical fungal infections occur. The topical composition of the present disclosure may also be applied to articles that come in contact with a topical fungal infection, such as, but not limited to, a pillow, bed sheets, stuffed toys, clothing, furniture, automobiles, a classroom environment, and the like.

Methods for reducing the incidence of or severity of a topical fungal infection and for preventing a topical fungal infection are also provided for by the present disclosure. One method for reducing the severity of a topical fungal infection generally comprises the steps of applying the topical composition of the present disclosure to the fungal infection. Preferably, the topical fungal infection is a fungal infection of the head or scalp. The method for preventing or treating topical fungal infections generally comprises the steps of applying the topical composition to areas of the body where topical fungal infections occur, most preferably on the scalp. The method for prophylaxis or treating a fungal infection provided by the present disclosure may also include application of the topical composition to articles that come into contact with a topical fungal infection, such as, but not limited to, a pillow, bed sheets, stuffed toys, clothing, furniture, automobiles, a classroom environment, and the like.

The present disclosure provides for an effective way to treat, manage, eradicate, and prevent topical fungal infections. Preferably, the fungal infection is tinea capitis, caused by *Trichophyton tonsurans* (*T. tonsurans*), however, other fungal infections are also envisioned. The compositions and methods provided by the present disclosure preferably treatment and/or prophylaxis of a topical fungal infection, reducing the number of fungal cells, minimizing or eliminating spore shedding, decreasing the spread of fungal infections, decreasing acquisition of fungal infections, decreasing susceptibility to fungal infections, decreasing the infection potential including preventing the spread of fungal infections to other children as well as further spreading on the same child, preventing fungal infections or re-infections, and combinations thereof. Preferably, the number of fungal cells is decreased by at least 50% after the statin composition of the present disclosure is applied.

The topical composition of the present disclosure preferably comprises an agent in an effective amount for the treatment and/or prevention of topical fungal infection. The effective amount of the agent, in some embodiments, can be combined with or incorporated into known lotion products, shampoo products, topical sprays, and the like. Alternatively, the topical composition of the present disclosure includes an effective amount of an agent and an amount of a carrier or vehicle. The amount of carrier or vehicle will depend on the route of administration of the topical composition. Components in addition to the agent may be present in the topical composition such as, but not limited to, fragrances, colors, foaming agents, and the like.

When compositions in accordance with the present disclosure are applied to articles that come into contact with a topical fungal infection, it is preferred that such compositions are environmentally safe and do not damage the article by discoloring it, modifying its appearance, or modifying its physical characteristics or integrity. Compositions that are sprayable are especially preferred for application to such articles.

Preferred agents of the disclosure are selected from the group consisting of HMG-CoA reductase inhibitors or statins, plant oils and/or extracts, and combinations thereof. Preferred statins include cerivastatin, itavastatin, pitavastatin, simvastatin, simvastatin acid, mevastatin, 3'-hydroxy simvastatin acid, 6'-hydroxymethyl simvastatin acid, lovastatin, atorvastatin, fluvastatin, pravastatin, rosuvastatin, active metabolites of any of the listed statins, or combinations thereof. In a most preferred embodiment, the statin is selected from the group consisting of cerivastatin, pitavastatin, and/or simvastatin acid. Preferred plant oils and/or extracts are selected from the group consisting of allspice (*Pimenta dioica*), anise (*Pimpinella anisum*), arachis (*Arachis hypogaea*), baobab (*Adansonia digitata*), basil (*Ocimum basilicum*), clove (*Ocimum gratissimum*), beach cabbage (*Scaevola sericea*), cassia bark, chinese (*Cinnamomum cassia*), celery seed (*Apium graveolens*), chives, garlic (*Allium tuberosum*), cinnamon (*Cinnamomum verum*), citronella (*Cymbopogon nardus*), citronella (*Cymbopogon winterianus*), clove (*Syzygium aromaticum*), coriander (*Coriandrum sativum*), eucalyptus (*Eucalyptus obliqua*), fennel (*Foeniculum vulgare*), fish poison tree (*Barringtonia asiatica*), garlic (*Allium sativum*), geranium (*Pelargonium hortorum*), juniper (*Juniperus communis*), kava kava (*Piper methysticum*), kopiko ula (*Psychotria hawaiiensis*), lavender (*Lavandula angustifolia*), lemon grass (*Cymbopogon citratus*), mamaki (*Pipturus albidus*), morning glories (*Ipomoea* sp.), mustard seed (*Brassica juncea*), myrtle (*Eugenia umbelliflora*), myrtle (*Pimenta racemosa*), olive (*Olea europaea*), orange (*Citrus sinensis*), oregano (*Origanum vulgare*) palmarosa (*Cymbopogon martini*), patchouli (*Pogostemon cablin*), peppermint (*Mentha piperita*), perilla (*Perilla frutescens*), rose apple bark (*Syzygium jambos*), rose apple, malay (*Eugenia malaccensis*), rosemary (*Rosemarinus officinalis*), shikakai (*Acacia concinna*), tea tree, lemon scented tea tree (*Leptospermum petersonii*), thyme (*Thymus vulgaris*), turpentine (*Pinus palustris*), and combinations thereof.

Carriers and vehicles useful with the present disclosure are preferably selected from the group of serum, cream, and ointment, and combinations thereof. Preferred serums include an ingredient selected from the group consisting of Alkyl Benzoate, Butylene Glycol, Cyclopentasiloxane, Cyclohexasiloxane, Dimethicone, Dimethiconol, Ethylhexyl Methoxycinnamate, Isodecyl Neopentanoate, Phenoxyethanol, and combinations thereof. Preferred creams include an ingredient selected from the group consisting of Aluminum Stearate, Acetamide MEA, Behentrimonium Methosulfate, Caprylyl Glycol, Cetyl Alcohol, Cetyl Esters, Cetearyl Alcohol, Glycerin, Hydroxyethylcellulose, Imidazolidinyl Urea, Isopropyl Lanolate, Lanolin, Methylparaben, Methylisothiazolinone, Mineral Oil, Phenoxyethanol, Peg-75, Polyquaternium 11, Polysorbate 20, PPG 10 Cetyl Ether, Propylparaben, Petrolatum, Polisorbate-60, Sodium Borate, Stearic Acid, Stearalkonium Chloride PA, and combinations thereof. Preferred ointments include an ingredient selected from the group consisting of Aluminum Stearate, Beeswax, Benzyl Alcohol, Benzyl Salicylate, Bis-Diglyceryl Polyacyladipate-2, Calcium Oxide, Carbomer, Caprylyl Glycol, Cetearyl, DMDM Hydantion, Glyeryl Stearate, Glycerin, Glycine, Imidazolidinyl Urea, Linalool, Mineral Oil, Oleth-5, Petrolatum, Peg-75, Polysorbate 80, PEG-40, Phenoxyethanol, Phenoxyethanol, Propylparaben, Shea butter, Stearic Acid, Sodium Cocoyl Glutamate, Triethanolamine, and combinations thereof.

DETAILED DESCRIPTION

The topical composition of the present disclosure preferably includes an amount of a statin or HMG-CoA reductase inhibitor, or the active metabolites thereof. Preferred statins include, but are not limited to, cerivastatin, itavastatin, pitavastatin, simvastatin, simvastatin acid, mevastatin, 3'-hydroxy simvastatin acid, 6'-hydroxymethyl simvastatin acid, lovastatin, atorvastatin, fluvastatin, pravastatin, rosuvastatin, any of the active metabolites of these preferred statins, or combinations thereof. In a most preferred embodiment, cerivastatin, pitavastatin, and/or simvastatin acid are used. The statins are preferably utilized in any form available for a statin, such as, but not limited to the acid or an active metabolite of a statin.

Preferably, the statin is present in the statin composition in an amount of from about 0.001% to 10% of the composition, more preferably from about 0.002% to 8% of the composition, more preferably from about 0.003% to 7% of the composition, still more preferably from about 0.004% to about 6.5% of the composition, still more preferably, from about 0.005% to about 6% of the composition, more preferably, from about 0.006% to about 5%, still more preferably from about 0.007% to about 4%, even more preferably, from about 0.008% to about 3%, still more preferably from about 0.009% to about 2% and most preferably from about 0.01% to about 1%, where values including, but not limited to, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, and 1% are also envisioned.

When the topical composition includes a statin, the topical composition is at least 5% more effective, more preferably at least 10% more effective, still more preferably at least 20% more effective, still more preferably at least 30% more effective, still more preferably at least 40% more effective, even more preferably at least 50% more effective, more preferably at least 60% more effective, still more preferably at least 75% more effective, even more preferably at least 80% more effective, more preferably at least 85% more effective, still more preferably at least 90%, even more preferably at least 95, 96, 97, 98, 99, or even 100% more effective at reducing the severity of a fungal infection, reducing the number of fungal cells, minimizing or eliminating spore shedding, decreasing the spread of fungal infections in a population, decreasing acquisition of fungal infections, decreasing susceptibility to fungal infections, decreasing the infection potential including preventing the spread of fungal infections to other children as well as further spreading on the same child, and preventing fungal infections or re-infections, wherein the increased effectiveness is in comparison to an individual that has not received a topical composition in accordance with the present disclosure. Further, 100% more effective means that the condition was completely eliminated or prevented. For example, spore shedding would be eliminated, fungal infections would not spread, fungal cells would be eliminated, and the like.

In a further aspect of the present the statin composition of the present disclosure further comprises an anti-fungal agent. The anti-fungal agent can be any agent known to have anti-fungal properties, or any agent that was determined by the present disclosure to have anti-fungal properties including polyene antifungals, allylamines, echinocandins, amphotericin B, benzoic acid, ciclopirox, flucytosine, haloprogin, tolnaftate, candicicin, filipin, hamycin, rimocidn, squalene epoxidase inhibitors, the agents found below in Table 1, azoles, nystatin, griseofulvin, terbinafine, primycin, and combinations thereof. Preferred azoles include ketoconazole, fluconazole, and itraconazole. Plant oils and/or extracts, as described above, can also be used as an anti-fungal agent. In a preferred embodiment, the anti-fungal agent is selected from, but not limited to, plant oils and/or extracts, griseofulvin, terbinafine, naftifine, miconazole, or combinations thereof.

Preferably, the anti-fungal agent is present in the statin composition in an amount of from about 0.001% to 10% of the composition, more preferably from about 0.002% to 8% of the composition, more preferably from about 0.003% to 7% of the composition, still more preferably from about 0.004% to about 6.5% of the composition, still more preferably, from about 0.005% to about 6% of the composition, more preferably, from about 0.006% to about 5%, still more preferably from about 0.007% to about 4%, even more preferably, from about 0.008% to about 3%, still more preferably from about 0.009% to about 2% and most preferably from about 0.01% to about 1%, where values including, but not limited to, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, and 1% are also envisioned.

In an embodiment where a statin and an anti-fungal agent are present in the composition, the topical composition is preferably more effective than when the topical composition includes a statin but does not include an anti-fungal agent. Preferably, the topical composition including a statin and an anti-fungal agent is at least 5% more effective, more preferably at least 10% more effective, still more preferably at least 20% more effective, still more preferably at least 30% more effective, still more preferably at least 40% more effective, even more preferably at least 50% more effective, more preferably at least 60% more effective, and most preferably at least 75% or more effective at reducing the severity of a fungal infection, reducing the number of fungal cells, minimizing or eliminating spore shedding, decreasing the spread of fungal infections in a population, decreasing acquisition of fungal infections, decreasing susceptibility to fungal infections, decreasing the infection potential including preventing the spread of fungal infections to other children as well as further spreading on the same child, and preventing fungal infections or re-infections, wherein the increased effectiveness is in comparison to a topical composition that includes a statin, but does not include the anti-fungal agent.

In another embodiment of the present disclosure, the topical composition of the present disclosure includes a statin that is incorporated into a pre-existing product. Preferably, the pre-existing products are selected from, but not limited to, serums, creams, ointments, lotions, gels, shampoo products, conditioners, soaps, sprays, oils, and combinations thereof. Creams, serums, and ointments are particularly preferred.

In another embodiment of the present disclosure, the topical composition includes a statin, as described above, in combination with plant oils and/or extracts, as described above. Such compositions are preferably included in the pre-existing products, as described above. Such an embodiment may further comprise an anti-fungal agent, as described above.

In an embodiment where the topical composition of the present disclosure includes a statin incorporated into a pre-existing product, the statin is present in an amount of from about 0.001% to 10% of the composition, more preferably from about 0.002% to 8% of the composition, more preferably from about 0.003% to 7% of the composition, still more preferably from about 0.004% to about 6.5% of the composition, still more preferably, from about 0.005% to about 6% of the composition, more preferably, from about 0.006% to about 5%, still more preferably from about 0.007% to about 4%, even more preferably, from about 0.008% to about 3%, still more preferably from about 0.009% to about 2% and most preferably from about 0.01% to about 1%, where values including, but not limited to, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, and 1% are also envisioned. Similarly, if an anti-fungal agent is included, it is also present in an amount of from about 0.001% to 10% of the composition, more preferably from about 0.002% to 8% of the composition, more preferably from about 0.003% to 7% of the composition, still more preferably from about 0.004% to about 6.5% of the composition, still more preferably, from about 0.005% to about 6% of the composition, more preferably, from about 0.006% to about 5%, still more preferably from about 0.007% to about 4%, even more preferably, from about 0.008% to about 3%, still more preferably from about 0.009% to about 2% and most preferably from about 0.01% to about 1%, where values including, but not limited to, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, and 1% are also envisioned. When plant oils and/or extracts are included in a composition that includes a statin and/or an anti-fungal agent, the plant oil and/or extract is present in an amount from about 0.001% to 50% of the composition, more preferably from about 0.01% to 40% of the composition, more preferably from about 0.1% to 30% of the composition, still more preferably from about 1% to about 20% of the composition, still more preferably, from about 1.5% to about 15% of the composition, and most preferably from about 2% to about 12%, where values including, but not limited to, 3%, 4%, 5%, 6%, 7%, 8%, 9%, 10%, and 11% are also envisioned.

In yet a further embodiment, the statin composition of the present disclosure additionally comprises a carrier or vehicle. Any carrier or vehicle suitable for topical administration will work for purposes of the present disclosure. Serums, creams, and ointments are preferred carriers or vehicles. As noted above, preferred serums include an ingredient selected from the group consisting of Alkyl Benzoate, Butylene Glycol, Cyclopentasiloxane, Cyclohexasiloxane, Dimethicone, Dimethiconol, Ethylhexyl Methoxycinnamate, Isodecyl Neopentanoate, Phenoxyethanol, and combinations thereof. Preferred creams include an ingredient selected from the group consisting of Aluminum Stearate, Acetamide MEA, Behentrimonium Methosulfate, Caprylyl Glycol, Cetyl Alcohol, Cetyl Esters, Cetearyl Alcohol, Glycerin, Hydroxyethylcellulose, Imidazolidinyl Urea, Isopropyl Lanolate, Lanolin, Methylparaben, Methylisothiazolinone, Mineral Oil, Phenoxyethanol, Peg-75, Polyquaternium 11, Polysorbate 20, PPG 10 Cetyl Ether, Propylparaben, Petrolatum, Polisorbate-60, Sodium Borate, Stearic Acid, Stearalkonium Chloride PA, and combinations thereof. Preferred ointments include an ingredient selected from the group consisting of Aluminum Stearate, Beeswax, Benzyl Alcohol, Benzyl Salicylate, Bis-Diglyceryl Polyacyladipate-2, Calcium Oxide, Carbomer, Caprylyl Glycol, Cetearyl, DMDM Hydantion, Glyeryl Stearate, Glycerin, Glycine, Imidazolidinyl Urea, Linalool, Mineral Oil, Oleth-5, Petrolatum, Peg-75, Polysorbate 80, PEG-40, Phenoxyethanol, Phenoxyethanol, Propylparaben, Shea butter, Stearic Acid, Sodium Cocoyl Glutamate, Triethanolamine, and combinations thereof. Preferably, the carrier or vehicle is present in the statin composition in an amount of from about 1% to 99.999% of the composition, more preferably from about 10% to 99.99% of the composition, more preferably from about 20% to 99.9% of the composition, still more preferably from about 30% to about 99.8% of the composition, still more preferably, from about 35% to about 99.7% of the composition, more preferably, from about 40% to about 99.6%, still more preferably from about 50% to 99.5%, more preferably from about 60% to 99.4% of the composition, still more preferably from about 70% to about 99.3% of the composition, still more preferably, from about 80% to about 99.2% of the composition, more preferably, from about 85% to about 99.1%, and most preferably from about 90% to 99%.

In another aspect of the present disclosure, a method for the reduction of the severity of a fungal infection is provided. The method of the present disclosure preferably includes the step of administering the topical composition of the present disclosure to a subject in need thereof. Preferably, the method additionally includes the step of administering the topical composition at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more times. This administration can be done more than once per day, or once every 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. Preferred administration schedules include a daily to weekly application for months, or even years. Preferably, the administration will continue until the individual is out of primary school. The method preferably includes the step of administering the topical composition to a location where it can contact a fungal infection or an area of the body susceptible to fungal infections. Most preferably, the method includes the step of applying the topical composition of the present disclosure to the head of a subject in need thereof. Additionally, the topical composition may be applied to articles that may come into contact with the fungal infection. The administration schedule for the article may be the same or different than the administration schedule to the location on the body. Further, the form of the topical composition may vary depending on whether the application is to an article or to a location on the body. For example, the topical composition for article administration might be in a sprayable form while the topical composition for the body might be in a cream.

In another aspect of the disclosure, the topical composition is administered in conjunction with or as an adjunct to existing treatment. In such situations, the individual has already been diagnosed with a topical fungal infection and is receiving some other form of treatment, such as oral medications, to combat the active infection. The topical composition is administered as described above in order to help with the treatment aspect. After the active infection is minimized or eliminated, the other treatment regimen can be discontinued while the topical composition of the present disclosure can be administered for its prophylactic benefits.

The methods of the present disclosure and topical composition of the present disclosure preferably reduce the severity of a fungal infection, reduce the number of fungal cells, minimize or eliminate spore shedding, decrease the spread of fungal infections in a population, decrease acquisition of fungal infections, decrease susceptibility to fungal infections, decrease the infection potential including preventing the spread of fungal infections to other children as well as further spreading on the same child, and prevent fungal infections or re-infections, wherein the increased effectiveness is in comparison to an individual or population that has not received a topical composition in accordance with the present disclosure. Preferably, each of these are improved by at least 10%, more preferably by at least 20%, more preferably by at least 30%, still more preferably by at least 40%, more preferably by at least 50%, still more preferably by at least 60%, even more preferably by at least 70%, more preferably by at least 80%, more preferably by at least 90%, and most preferably by 100%. One of skill in the art can determine appropriate methods of comparison in order to determine the percentage of improvement. For example, for reducing the number of fungal cells, an improvement of 10% would mean that the individual being administered the topical composition of the present disclosure had 10% fewer fungal cells than an individual not receiving an administration of the topical composition. Similarly, for decreasing the spread of fungal infections in a population, populations receiving the administration of the topical composition of the present disclosure would preferably have at least 10% fewer fungal infections than a population that did not receive the administration of the topical composition.

In another aspect of the disclosure, use of the topical composition on individuals taking another form of treatment, such as oral medications, for the treatment of fungal infections will permit lower amounts or dosages of the other treatment to be administered and maintain the same level of effectiveness as the higher dosage. Preferably, the amounts or dosages of the other treatments will be able to be decreased by at least 10%, more preferably by at least 20%, more preferably by at least 30%, still more preferably by at least 40%, more preferably by at least 50%, still more preferably by at least 60%, even more preferably by at least 70%, and most preferably by at least 80%.

In another aspect of the disclosure, use of statins and an anti-fungal agent in the topical composition will permit lower amounts of at least one of the individual active ingredients (i.e. the statin and the anti-fungal) to be used but still maintain the effectiveness of the higher dosage when the statin or anti-fungal agent are used alone. Preferably, the amount or dosage of at least one of the active ingredients will be able to be reduced by at least 10%, more preferably by at least 20%, more preferably by at least 30%, still more preferably by at least 40%, more preferably by at least 50%, still more preferably by at least 60%, even more preferably by at least 70%, and most preferably by at least 80%.

In yet another aspect of the present disclosure, a method for preventing fungal infections is provided. The method preferably includes the step of administering the topical composition of the present disclosure to a subject in need thereof. Preferably, the method additionally comprises the step of administering the topical composition multiple times, as described above. The method preferably includes the step of administering the topical composition to a location where fungal infections generally occur or to an area of the body susceptible to fungal infections. Most preferably, the method includes the step of applying the topical composition of the present disclosure to the head of a subject in need thereof. In an alternate embodiment, the method additionally includes the step of administering the topical composition to areas that may contact a topical fungal infection, such as, but not limited to, a pillow, hat, hairbrush, bed sheets, clothing, stuffed toy, furniture, car seat, classroom environment, and the like.

Embodiments of the present disclosure can be used to treat, reduce the incidence of, or prevent fungal infections. In preferred forms, the methods and compositions of the present disclosure can be used to treat, reduce the incidence of, or prevent dermatophyte infection. Preferably, the methods and compositions of the present disclosure can be used to treat, reduce the incidence of, or prevent Tinea barbae, Tinea captitis, Tinea corporis, Tinea cruris, Tinea manuum, Tinea pedis, Tinea unguiuum, Onychomycosis, Tinea corporis gladitorum, Tinea faciei, Tinea imbricate, Tinea incognito, Favus or the organisms *Epidermophyton floccosum, Microsporum canis, Microsporum audouinii, Trichophyton interdigitale, Trichophyton mentagrophytes, Trichophyton tonsurans (T. tonsurans), Trichophyton schoenleini, Trichophyton rubrum, Trichophyton equinum*. Of these, Tinea capitis and *T. tonsurans* are preferred targets for the composition and methods described herein.

Preferably, the method of the present disclosure and topical composition of the present disclosure preferably prevent fungal infection noted above or caused by the dermatophytes described herein. In preferred forms, the dermatophytes are selected from those listed above. In the case of Tinea capitis and *T. tonsurans*, the method prevents *T. tonsurans* from growing on the scalp. In a group or, by way of example, in a classroom setting, *T. tonsurans* infection is decreased by at least 10%, more preferably by at least 20%, more preferably by at least 30%, still more preferably by at least 40%, more preferably by at least 50%, still more preferably by at least 60%, even more preferably by at least 70%, more preferably by at least 80%, more preferably by at least 90%, and most preferably by 95% of the individuals in a group or classroom. This decrease or reduction is in comparison to a group or classroom that is not being treated as described herein.

The present disclosure also provides for a method of reducing the fungal cells on the scalp of an individual in need thereof. Such a method reduces the overall fungal burden and/or decreases the amount or number of growing spores. The method generally includes the steps of administering the topical composition of the present disclosure to the scalp of an individual in need thereof. The method preferably reduces the number of fungal cells on the scalp by at least 10%, more preferably by at least 20%, more preferably by at least 30%, still more preferably by at least 40%, more preferably by at least 50%, still more preferably by at least 60%, even more preferably by at least 70%, more preferably by at least 80%, more preferably by at least 90%, and most preferably by 100%.

The present disclosure further provides a topical composition effective for reducing the severity of fungal infections to a point below where symptoms are evident and the infection does not develop or progress to the point of exhibiting symptoms of fungal infection.

EXAMPLES

Example 1

This example illustrates the mechanism by which statin activity is tested.

Materials and Methods

Isolation of Spores:

Materials Used:
- 10 mm×100 mm petri plate of dermatophyte culture grown to confluency (>14 days) on Sabouraud's dextrose agar (Becton Dickinson, Sparks Md.) containing 50 mg/L chloramphenicol and 500 mg/L cycloheximide (Sigma Chemical Company, St. Louis Mo.) (see appendix A for recipe).
- 1× sterile Phosphate Buffered Saline (Sigma Chemical Company, St. Louis Mo.).
- (2) 15 mL sterile disposable conical tubes (Thermo Fisher Scientific, Rochester N.Y.).
- Disposable sterile inoculating loop (Fisher Scientific, Hanover Park Ill.).
- Disposable sterile transfer pipette (Fisher Scientific, Hanover Park Ill.).
- Sterilized 2"×2" 4 ply gauze (Medline Industries, Mundelein Ill.)
- 30 mL sterile disposable syringe (Becton Dickinson, Franklin Lakes N.J.).
- Hemocytometer (Fisher Scientific, Hanover Park Ill.).

Spore Prep Procedure (performed aseptically in a biosafety cabinet):

The fungal plate was flooded with 10 mL of sterile 1×PBS and with a sterile disposable inoculating loop, then the surface was gently scraped until all the fungal material (hyphae and spores) was liberated into the PBS.

Using a disposable transfer pipette, the entire volume of PBS/spores was transferred from the plate into a sterile 15 mL conical tube.

Next, 2 mL of sterile 1×PBS was added to the plate and swirled to rinse.

Using the transfer pipette, the remaining volume of PBS/spores was transferred from the plate to the 15 mL conical.

Then, the 15 mL tube was capped and vortexed at max speed for 10-15 seconds, set aside.

The plunger from the 30 mL syringe was then removed and the barrel was packed with 1 square of sterile 2"×2" gauze.

Using the plunger, the gauze was firmly packed at the bottom of the barrel then the plunger was removed.

The syringe barrel was placed into a new sterile 15 mL conical tube and the entire contents of the 15 mL PBS/spore suspension was poured directly onto the gauze in the syringe barrel.

The plunger was then gently inserted into the barrel and depressed all the way down to filter the spore/hyphal suspension through the gauze.

The plunger was gently removed and additional 2 mL of sterile PBS was added back to the original 15 mL conical tube. The contents was vortexed briefly and poured into the syringe barrel.

The filtering process was then repeated and flow collected through into the "filtered" 15 mL conical.

The spores were then counted using standard methods with the hemocytometer.

They were then diluted to make 10 mL of a 1×106 spores/mL.

The tubes were then stored at 4° C. and used within 24 hours.

Screening (384 well format):

This procedure assumed the library of compounds to be tested had been pre-spotted into the 384 well plates. Note: final concentration of DMSO was not to exceed 0.5%.

Materials Required:
- A fresh dermatophyte spore preparation @ 1×106 spores/mL
- 1× sterile Phosphate Buffered Saline (Sigma Chemical Company, St. Louis Mo.).
- 2× Sabouraud's Dextrose Broth (Becton Dickinson, Sparks Md.)—Sterile (see appendix A).
- 384 well sterile black culture plate(s) with optically clear bottoms (Thermo Scientific, Rochester N.Y.) spotted with compounds to be tested.
- Automated fluid dispenser
- Microplate reader capable of reading at 600 nM.
- Sterile glass Erlenmeyer flask.
- EDGE® seals (EDGEbio, Gaithersburg, Md.).

Procedure:

For each 384 well plate to be tested, 4 mL of the spore suspension was mixed with 10 mL of 1×PBS (this resulted in an absolute number of 104 spores in 35 µL dispensed per well). NOTE: there was residual spore suspension, the calculations above allowed for overage to ensure enough suspension is made for each plate.

Using the peristaltic pump, the automated dispenser was programmed to deliver 35 µL of 2×SabDEX broth to each well in the 384 well plate. The pump was then purged of growth media and re-primed with the spore suspension. The dispenser was then programmed to deliver 35 µL of spore suspension to each test well (to include+growth controls).

Negative growth controls were made by manually pipetting 35 µL of sterile 1×PBS from a sterile multichannel boat into each (−) control well using a 100 µL pipette.

Each plate was given a numerical designation, dated, sealed with an EDGE® seal and placed in a 32° C. incubator for 48 hours.

After incubation, the seal was carefully removed and the plate read at 600 nM using a single point read on a microplate reader.

If more time was required, the plate was re-sealed and incubated an additional 24 hours.

MIC Testing (96 well format):

Materials Required:
- Dermatophyte spore prep @ 1×106 spores/mL (see above).
- Sterile 96 well flat bottomed clear culture plate (Falcon 1172, Becton Dickinson Labware, Franklin Lakes N.J.).
- 2× Sabouraud's Dextrose Broth (Becton Dickinson, Sparks Md.)—Sterile (see appendix A).
- 2×RPMI-1640 Culture Media (Sigma Chemical Company, St. Louis Mo.)—Sterile
- 2× Keratin Media.
- 2× Culture Medium—Sterile, containing 1.0% DMSO.
- 1× sterile Phosphate Buffered Saline (Sigma Chemical Company, St. Louis Mo.).
- Drug to be tested (identified from previous screening) dissolved in 100% DMSO (Sigma Chemical Company, St. Louis Mo.).

Sterile 1.5 mL disposable microfuge tubes (Midwest Scientific, St. Louis Mo.).

Multichannel pipette capable of delivering 100 µL volumes.

Sterile liquid reservoirs for holding spore/PBS solution (Midwest Scientific, St. Louis Mo.).

100 µL manual pipetteman.

15 mL conical tubes (Thermo Fisher Scientific, Rochester N.Y.).

EDGE® seals (EDGEbio, Gaithersburg, Md.).

General Procedure for MIC testing of compounds ranging from 10 µM (high standard) to 0.01 µM (low standard) (this may require modification based on media used, concentration ranges of compounds being tested and/or solvents used).

To Make the Spore Suspension:

Combined 0.4 mL of a 1×106 spore preparation with 3.6 mL sterile 1× sterile PBS in a 15 mL conical tube and vortexed to mix well.

To Make Drug Dilutions:

A 2 mM stock of the compound to be tested was made in 100% DMSO in a sterile 1.5 mL microfuge tube.

Vortexed the tube vigorously for 1 minute, then protected the compound from light and rocked or shook for 1 hour at room temperature to fully dissolve.

NOTE: Because the 2× culture media was diluted with an equal volume of spore/PBS solution to achieve a 1× final media concentration, the high standard for the range of compound to be tested was made at 2× the highest concentration desired and contain a final DMSO concentration of 0.5%.

To generate the range of compound to be tested, the following dilution protocol was performed:

(a) The high standard was made:

| 20 µM * 1000 µl = | 10 uL of the 2 µM drug stock |
| 2000 µM | 990 µL 2× Culture Medium |

The result was 1000 µL of a 20 µM stock in 2× Culture Medium with a final [DMSO] of 1%.

(b) The drug dilution range to be tested was made by serially diluting the high standard 1:1 with 2× Culture Medium/1% DMSO.

Figure 1:
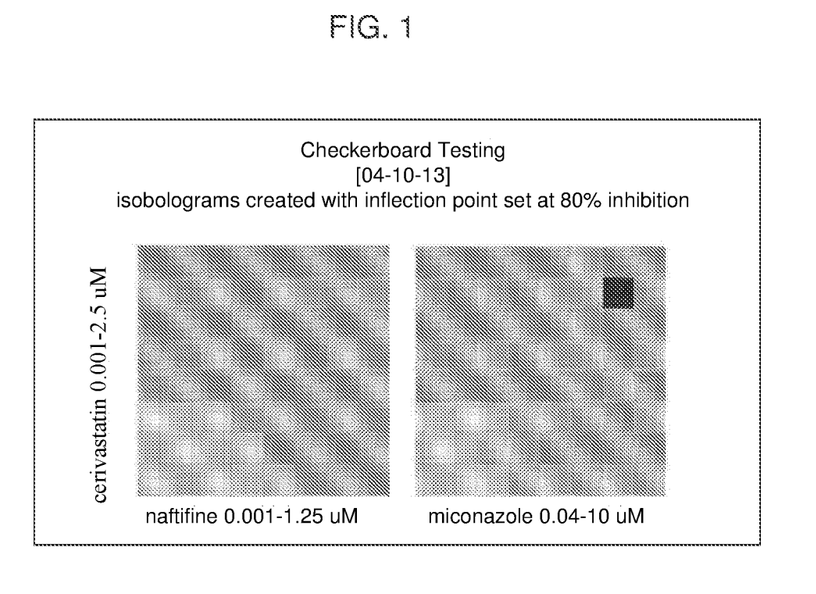
FIG. 1 is a representation of isobolograms depicting the synergistic activity of cerivastatin in combination of naftifine or miconazole at varying concentrations.
Figure 2:
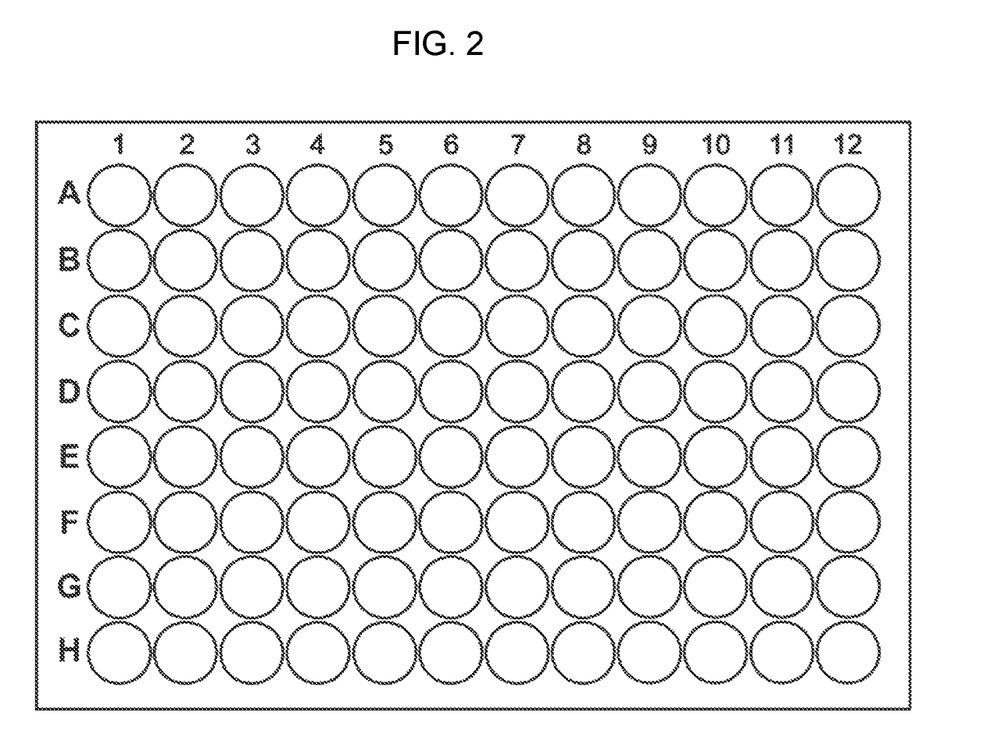
FIG. 2 is a plate map of a multi-well plate used in the Examples.

Aseptically added 100 µL of the drug/media manually to each well according to the plate map in FIG. 2, as follows:

A1, B1, C1=100 µl of the 20 µM high standard
A2, B2, C2=100 µL of the 10 µM
A3, B3, C3=100 µL of the 5 µM
A4, B4, C4=100 µL of the 2.5 µM
A5, B5, C5=100 µL of the 1.25 µM
A6, B6, C6=100 µL of the 0.625 µM
A7, B7, C7=100 µL of the 0.3125 µM
A8, B8, C8=100 µL of the 0.156 µM
A9, B9, C9=100 µL of the 0.078 µM
A10, B10, C10=100 µL of the 0.04 µM
A11, B11, C11=100 µL of the 0.02 µM
A12, B12, C12=100 µL of the 0 µM (this serves as no drug+growth controls)
G1-G6=100 µL of 2× Culture medium containing 1% DMSO At this point, if more than (1) compound was being tested, a second MIC series was added to rows D, E, and F in the same format as done for rows A, B, and C.

Manually added 100 µL of sterile 1×PBS to wells G1-G6 to generate the (−) growth controls.

Vortexed the spore suspension for 10 seconds and then added 1004, to rows A, B, and C using a multichannel pipette man.

Sealed the plate with an EDGE seal and incubated @ 32° C. for a minimum of 48 hours.

After 48 hours of incubation, carefully removed the plate seal and read the absorbance at 600 nM using a 5×5 area scan protocol on a plate reader.

Checkerboard Testing (96 well format):

Materials Required:

Dermatophyte spore prep @ 1×106 spores/mL (see above for protocol).

Sterile 96 well flat bottomed clear culture plate (Falcon 1172, Becton Dickinson Labware, Franklin Lakes N.J.).

2× Sabouraud's Dextrose Broth (Becton Dickinson, Sparks Md.)—Sterile (see appendix A).

2×RPMI-1640 Culture Media (Sigma Chemical Company, St. Louis Mo.)—Sterile (See appendix A).

2× Keratin Media (see appendix A).

2× Culture Medium—Sterile, containing 1.0% DMSO (see appendix A).

1× sterile Phosphate Buffered Saline (Sigma Chemical Company, St. Louis Mo.).

Drug to be tested (identified from previous screening) dissolved in 100% DMSO (Sigma Chemical Company, St. Louis Mo.).

Sterile 1.5 mL disposable microfuge tubes (Midwest Scientific, St. Louis Mo.).

Multichannel pipette capable of delivering 100 µL volumes.

Sterile liquid reservoirs for holding spore/PBS solution (Midwest Scientific, St. Louis Mo.).

100 µL manual pipetteman.

15 mL conical tubes (Thermo Fisher Scientific, Rochester N.Y.).

EDGE® seals (EDGEbio, Gaithersburg, Md.).

To make the spore suspension: Combined 0.4 mL of a 1×106 spore preparation with 3.6 mL sterile 1× sterile PBS in a 15 mL conical tube and vortex to mix well.

To make drug dilutions:

A 4 mM stock of the compound to be tested in 100% DMSO was made in a sterile 1.5 mL microfuge tube.

The compound was then vortexed in the tube vigorously for 1 minute, then protected from light and rocked or shook for 1 hour at room temperature to fully dissolve.

NOTE: Because the 2× culture media is diluted with an equal volume of spore/PBS solution to achieve a 1× final media concentration and 2 drug concentrations are being tested, the high standard for the range of compound to be tested must be made at 4× the highest concentration desired and contain a final DMSO concentration of 0.5%.

To generate the range of compound to be tested, the following dilution protocol is performed:

(a) The high standard was made for each drug in the combination being tested:

| 40 µM * 1000 µl = | 10 µL of the 4 µM drug stock |
| 2000 µM | 990 µL 2× Culture Medium |

The result was 1000 µL of a 40 µM stock in 2× Culture Medium with a final [DMSO] of 1%.

(b) The drug dilution range to be tested was then generated by serially diluting the high standard 1:1 with 2× Culture Medium/1% DMSO.

Aseptically, 50 µL of each drug/media was manually added to each well according to the plate map in FIG. 2 as follows:

A1-8=50 µl of the 20 µM drug A, 1 A-H 50 µl of the 20 µM drug B

B1-8=50 µL of the 10 µM drug A, 2 A-H 50 µl of the 10 µM drug B

C1-8=50 µL of the 5 µM drug A, 3 A-H 50 µl of the 5 µM drug B

D1-8=50 µL of the 2.5 µM drug A, 4 A-H 50 µl of the 2.5 µM drug B

E1-8=50 µL of the 1.25 µM drug A, 5 A-H 50 µl of the 1.25 µM drug B

F1-8=50 µL of the 0.625 µM drug A, 6 A-H 50 µl of the 0.625 µM drug B

G1-8=50 µL of the 0.3125 µM drug A, 7 A-H 50 µl of the 0.3125 µM drug B

H1-8=50 µL of the 0.156 µM drug A, 8 A-H 50 µl of the 0.156 µM drug B

11 A-H=100 µL of the 0.00 µM (this serves as no drug+growth controls)

12 A-H=100 µL of 2× Culture medium containing 1% DMSO

Next, 100 µL of sterile 1×PBS was manually added to wells G1-G6 to generate the (−) growth controls.

The spore suspension was vortexed for 10 seconds and then 100 µL was added to rows A, B, and C using a multichannel pipette man.

The plate was sealed with an EDGE seal and incubated @ 32° C. for a minimum of 48 hours.

After 48 hours of incubation, the plate seal was carefully removed and the absorbance was read at 600 nM using a 5×5 area scan protocol on a plate reader.

Results and Conclusions:

TABLE 1

Rank order of the activity of selected HMG-CoA reductase inhibitors against a reference strain of *T. tonsurans* among the top 1% compounds from a preliminary screen of 7,676 compounds.

| Compound | DR Plate | Row | Prelim H ratio | Prelim L ratio | upper asymptote | rMIC50 mcM |
|---|---|---|---|---|---|---|
| Liranaftate | DR14 | A | 1.01 | 2.00 | 98.3 | <0.01 |
| Itraconazole | DR13 | B | 1.00 | 1.85 | 96.4 | <0.01 |
| Adefovir dipivoxil | DR16 | F | 1.06 | 2.18 | 94.9 | <0.01 |
| Sulconazole nitrate | DR14 | F | 1.01 | 2.00 | 94.6 | <0.01 |
| Oxiconazole Nitrate | DR13 | H | 1.01 | 2.00 | 94.1 | <0.01 |
| KU0163477 Synthesized by J. Aube | DR7 | D | | | 91.6 | <0.01 |
| Cerivastatin | DR7 | F | 1.06 | 2.28 | 91.3 | <0.01 |
| Oxiconazole | DR8 | E | 0.93 | 1.75 | 90.4 | <0.01 |
| Butoconazole nitrate | DR12 | D | 1.02 | 1.88 | 88.6 | <0.01 |
| Econazole nitrate | DR12 | B | 1.05 | 2.06 | 88.5 | <0.01 |
| Terbinafine | DR7 | G | 1.04 | 2.25 | 88.1 | <0.01 |
| Posaconazole | DR16 | E | 1.00 | 2.04 | 86.1 | <0.01 |
| Phenylmercuric acetate | DR2 | G | 1.06 | 2.17 | 84.1 | <0.01 |
| Butenafine Hydrochloride | DR13 | G | 1.00 | 1.85 | 83.9 | <0.01 |
| Tolnaftate | DR11 | C | 1.01 | 1.99 | 87.8 | 0.013 |
| Miconazole | DR11 | B | 1.07 | 2.09 | 92.5 | 0.014 |
| Thimerosal | DR14 | C | 1.03 | 2.03 | 90.4 | 0.017 |
| Itavastatin (Pitavastatin) Ca | DR10 | B | 1.04 | 2.00 | 97 | 0.018 |
| Tioconazole | DR10 | H | 1.03 | 2.02 | 95.1 | 0.018 |
| Ketoconazole | DR12 | H | 1.00 | 1.85 | 91.9 | 0.019 |
| Sertaconazole nitrate | DR15 | E | 1.00 | 2.01 | 71.9 | 0.019 |
| Isoconazole | DR11 | A | 1.05 | 2.06 | 100 | 0.022 |
| Atovaquone | DR7 | E | 0.44 | 0.95 | 64.8 | *0.033 |
| Bifonazole | DR16 | B | 1.06 | 2.12 | 97.6 | 0.038 |
| Fluvastatin sodium salt | DR15 | B | 1.03 | 2.03 | 93.4 | 0.043 |
| Enilconazole | DR15 | D | 0.97 | 1.95 | 92.5 | 0.046 |
| Hexachlorophene | DR16 | C | 1.02 | 2.05 | 92.7 | 0.056 |
| Clotrimazole | DR11 | G | 1.03 | 2.02 | 85.3 | 0.070 |
| Tetrachloroisophthalonitrile | DR5 | D | 1.10 | 2.21 | 95.1 | 0.073 |
| Naftifine hydrochloride | DR15 | F | 1.02 | 2.05 | 91.7 | 0.075 |
| Broxyquinoline | DR3 | H | 0.77 | 1.40 | 94.6 | 0.082 |
| Clioquinol | DR14 | G | 0.98 | 1.93 | 84.9 | 0.083 |
| Voriconazole | DR13 | D | 1.00 | 1.85 | 95.5 | 0.084 |
| KU0044883 Synthesized by C. Spelling | DR5 | F | 1.14 | 2.29 | 99.1 | 0.088 |
| Flutrimazole | DR5 | A | | | 100 | 0.089 |
| Temsirolimus | DR16 | D | 0.39 | 0.80 | 73.3 | 0.091 |
| Niclosamide | DR10 | F | 1.08 | 2.13 | 95.6 | 0.113 |
| KU0157581 Synthesized by J. Aube | DR6 | C | 1.03 | 2.00 | 100 | 0.117 |
| Ebselen | DR14 | B | 0.54 | 1.07 | 95.2 | 0.179 |
| Triclabendazole | DR9 | B | 1.07 | 2.14 | 96.2 | 0.212 |
| Chloroxine | DR11 | E | 1.01 | 1.99 | 89.7 | 0.220 |
| Disulfiram | DR10 | E | 0.46 | 0.91 | 100 | 0.227 |
| Simvastatin | DR15 | C | 1.01 | 2.00 | 85.7 | 0.248 |
| Bleomycin | DR4 | G | 0.40 | 0.74 | 93.1 | 0.263 |
| Flavokawain B | DR4 | B | 0.45 | 0.95 | 57 | *0.290 |
| Dequalinium dichloride | DR12 | G | 1.02 | 1.88 | 80.7 | 0.334 |
| Deguelin | DR4 | A | 0.48 | 0.87 | 100 | 0.335 |
| Haloprogin | DR12 | C | 1.04 | 1.91 | 89.3 | 0.345 |
| Closantel | DR13 | A | 0.61 | 1.13 | 100 | 0.368 |
| Cetrimonium bromide | DR5 | B | 1.04 | 1.91 | 97.7 | 0.390 |
| Pyrvinium pamoate | DR15 | G | 0.88 | 1.77 | 87 | 0.415 |
| Alexidine dihydrochloride | DR14 | D | 1.04 | 2.07 | 96 | 0.435 |

TABLE 1-continued Rank order of the activity of selected HMG-CoA reductase inhibitors against a reference strain of *T. tonsurans* among the top 1% compounds from a preliminary screen of 7,676 compounds.

| Compound | DR Plate | Row | Prelim H ratio | Prelim L ratio | upper asymptote | rMIC50 mcM |
|---|---|---|---|---|---|---|
| Digitonin | DR3 | D | 1.10 | 1.99 | 94.8 | 0.458 |
| Tomatidine HCl | DR3 | B | 0.45 | 0.92 | 97.1 | 0.486 |
| Mitotane | DR15 | H | 0.82 | 1.65 | 100 | 0.506 |
| Mycophenolic acid | DR3 | E | 0.45 | 0.82 | 93.7 | 0.517 |
| Anethole-trithione | DR8 | A | 0.79 | 1.70 | 100 | 0.529 |
| Griseofulvin | DR12 | A | 0.71 | 1.40 | 96.5 | 0.532 |
| Miltefosine | DR7 | H | 1.08 | 2.32 | 88.2 | 0.535 |
| Myclobutanil | DR8 | D | 0.76 | 1.43 | 100 | 0.537 |
| Auranofin | DR14 | H | 0.92 | 1.82 | 94.3 | 0.580 |
| Ampicillin trihydrate | DR10 | G | 0.40 | 0.78 | 91.8 | 0.585 |
| Climbazole | DR8 | B | 0.80 | 1.51 | 100 | 0.634 |
| Thonzonium bromide | DR15 | A | 1.06 | 2.11 | 95.1 | 0.637 |
| Terconazole | DR13 | C | 0.69 | 1.28 | 100 | 0.644 |
| mevastatin | DR10 | C | 0.45 | 0.86 | 86.4 | 0.650 |
| Triclosan | DR16 | A | 1.04 | 2.08 | 100 | 0.656 |
| Lovastatin | DR13 | E | 0.75 | 1.39 | 90.7 | 0.708 |
| Dichlorophene | DR3 | A | 1.08 | 2.21 | 100 | 0.709 |
| Honokiol | DR9 | A | 0.49 | 0.98 | 100 | 0.737 |
| Pterostilbene | DR9 | D | 0.71 | 1.42 | 100 | 0.826 |
| Dihydrotenone | DR3 | C | 0.53 | 1.08 | 100 | 0.855 |
| Ipriflavone | DR9 | E | | | 100 | 0.866 |
| Homidium bromide | DR4 | H | 0.87 | 1.59 | 91 | 0.885 |
| Chlorhexidine | DR11 | D | 0.95 | 1.86 | 100 | 0.912 |

TABLE 2

Investigation of the activity of selected HMG-CoA reductase inhibitors and their metabolites against a reference strain of *T. tonsurans*.

| | $IC_{50}$ (mcM) [range] |
|---|---|
| cerivastatin | 0.01 [0.003-0.058] |
| pitavastatin | 0.03 [0.003-0.032] |
| simvistatin acid | 0.03 [0.024-0.062] |
| atorvastatin | 0.14 |
| rosuvastatin | 0.19 |
| fluvastatin | 0.26 |
| mevastatin | 0.65 |
| lovastatin | 0.71 |
| simvistatin | 1.14 |
| 3"-hydroxy simvistatin acid | 1.92 |
| 6'-hydroxymethyl simvistatin acid | 2.07 |
| pravastatin | >10 |
| 3"-hydroxy simvistatin | NA |
| 3',5'-dihydrodiol simvistatin | NA |
| 6'-hydroxymethyl simvistatin | NA |

TABLE 3

Investigation of the activity of selected HMG-CoA reductase inhibitors/metabolites against 5 genetically distinct strain of *T. tonsurans*.

| $IC_{50}$ (mcM) | cerivastatin | pitavastatin | simvistatin acid |
|---|---|---|---|
| 1119-0616 | 0.010 | 0.027 | 0.062 |
| 0924-1093 | 0.005 | 0.018 | 0.050 |
| 0924-1456 | 0.015 | 0.024 | 0.052 |
| 0924-0254 | 0.003 | 0.003 | 0.029 |
| 0924-1669 | 0.005 | 0.025 | 0.052 |

TABLE 4

Investigation of the activity of selected HMG-CoA reductase inhibitors/metabolites against different *Trichophyton* species.

| $IC_{50}$ (mcM) | cerivastatin | pitavastatin | simvistatin acid |
|---|---|---|---|
| *T. rubrum* | 0.068 | 0.147 | 0.303 |
| *T. equinum* | 0.021 | 0.054 | 0.086 |
| *T. mentagrophytes* | 0.019 | 0.035 | 0.071 |

The invention claimed is:

1. A method for reducing the incidence or severity of a topical fungal infection caused by *Trichophyton tonsurans*, comprising:

topically applying a topical composition to an area where topical fungal infections of *Trichophyton tonsurans* occur on a subject in need thereof, said topical composition comprising:

an HMG-CoA reductase inhibitor selected from the group consisting of pitavastatin, atorvastatin, rosuvastatin, Fluvastatin, mevastatin, lovastatin, simvastatin, simvistatin acid, 3'-hydroxy simvastatin acid, 6'-hydroxymethyl simvistatin acid, and combinations thereof; and a carrier selected from the group consisting of serum, cream, ointment, lotion, gel, shampoo, hair conditioner, soap, oil, and combinations thereof.

2. The method of claim 1, wherein said topical composition is applied to the skin and/or hair on the head of said subject.

3. The method of claim 1, wherein said fungal infection is Tinea capitis.

4. The method of claim 1, wherein the topical composition is applied more than once.

5. The method of claim 1, wherein application of the topical composition reduces the number of growing spores of the fungus by at least 10%.

6. The method of claim 1, wherein the topical composition is applied to an area where topical fungal infections occur prior to fungal spores being present on said area.

7. The method of claim 1, wherein the carrier is a serum including an ingredient selected from the group consisting of Alkyl Benzoate, Butylene Glycol, Cyclopentasiloxane, Cyclohexasiloxane, Dimethicone, Dimethiconol, Ethylhexyl Methoxycinnamate, Isodecyl Neopentanoate, Phenoxyethanol, and combinations thereof.

8. The method of claim 1, wherein the carrier is a cream including an ingredient selected from the group consisting of Aluminum Stearate, Acetamide MEA, Behentrimonium Methosulfate, Caprylyl Glycol, Cetyl Alcohol, Cetyl Esters, Cetearyl Alcohol, Glycerin, Hydroxyethylcellulose, Imidazolidinyl Urea, Isopropyl Lanolate, Lanolin, Methylparaben, Methylisothiazolinone, Mineral Oil, Phenoxyethanol, Peg-75, Polyquaternium 11, Polysorbate 20, PPG 10 Cetyl Ether, Propylparaben, Petrolatum, Polisorbate-60, Sodium Borate, Stearic Acid, Stearalkonium Chloride PA, and combinations thereof.

9. The method of claim 1, wherein the carrier is an ointment including an ingredient selected from the group consisting of Aluminum Stearate, Beeswax, Benzyl Alcohol, Benzyl Salicylate, Bis-Diglyceryl Polyacyladipate-2, Calcium Oxide, Carbomer, Caprylyl Glycol, Cetearyl, DMDM Hydantion, Glyeryl Stearate, Glycerin, Glycine, Imidazolidinyl Urea, Linalool, Mineral Oil, Oleth-5, Petrolatum, Peg-75, Polysorbate 80, PEG-40, Phenoxyethanol, Phenoxyethanol, Propylparaben, Shea butter, Stearic Acid, Sodium Cocoyl Glutamate, Triethanolamine, and combinations thereof.

10. The method of claim 1, wherein said HMG-CoA reductase inhibitor is present in an amount from about 0.001% to 10% by weight of the composition.

11. The method of claim 1, wherein application of the topical composition results in a benefit selected from the group consisting of reducing the severity of a fungal infection, reducing the number of fungal cells, minimizing or eliminating spore shedding, decreasing the spread of fungal infections in a population, decreasing acquisition of fungal infections, decreasing susceptibility to fungal infections, decreasing the infection potential including preventing the spread of fungal infections to other children as well as further spreading on the same child, preventing fungal infections or re-infections, and combinations thereof.

12. The method of claim 1, wherein said subject has been administered another form of treatment for the fungal infection, wherein the application of the topical composition is occurring concurrently with the other form of treatment.

13. The method of claim 12, wherein the other form of treatment is oral medication.

14. The method of claim 12, wherein the amount of the other form of treatment is reduced by at least 10% when the topical administration and the other form of treatment are used together.

15. The method of claim 12, wherein the other form of treatment is in the form of an oral medication having an active ingredient therein, and wherein the amount of the active ingredient in the oral medication can be reduced by at least 10% while maintaining the same level of effectiveness.

16. The method of claim 1, said topical composition further comprising an anti-fungal agent.

17. The method of claim 16, wherein the anti-fungal agent is selected from the group consisting of polyene antifungals, allylamines, echinocandins, amphotericin B, benzoic acid, ciclopirox, flucytosine, haloprogin, tolnaftate, candicicin, filipin, hamycin, rimocidn, squalene epoxidase inhibitors, liranaftate, adefovir dipivoxil, KU0163477, phenylmercuric acetate, butenafine hydrochloride, tolnaftate, thimerosal, atovaquone, hexachlorophene, tetrachloroisophthalonitrile, naftifine hydrochloride, broxyquinoline, clioquinol, KU0044883, temsirolimus, niclosamide, KU0157581, ebselen, chloroxine, disulfiram, bleomycin, flavokawain B, dequalinium dichloride, deguelin, closantel, cetrimonium bromide, pyrvinium pamoate, alexidine dihydrochloride, digitonin, tomatidine HCl, mitotane, mycophenolic acid, anethole-trithione, miltefosine, myclobutanil, auranofin, ampicillin trihydrate, thonzonium bromide, triclosan, dichlorophene, honokiol, pterostilbene, dihydrotenone, ipriflavone, homidium bromide, chlorhexidine, azoles, nystatin, griseofulvin, terbinafine, primycin, plant oils and/or extracts, and combinations thereof.

18. The method of claim 16, wherein the anti-fungal agent is selected from the group consisting of plant oils and/or extracts, griseofulvin, terbinafine, naftifine, miconazole, and combinations thereof.

19. The method of claim 18, wherein the plant oil or extract is derived from a plant selected from the group consisting of allspice (*Pimenta dioica*), anise (*Pimpinella anisum*), arachis (*Arachis hypogaea*), baobab (*Adansonia digitata*), basil (*Ocimum basilicum*), clove (*Ocimum gratissimu*), beach cabbage (*Scaevola sericea*), cassia bark, chinese (*Cinnamomum cassia*), celery seed (*Apium graveolens*), chives, garlic (*Allium tuberosum*), cinnamon (*Cinnamomum verum*), citronella (*Cymbopogon nardus*), citronella (*Cymbopogon winterianu*), clove (*Syzygium aromaticum*), coriander (*Coriandrum sativum*), eucalyptus (*Eucalyptus obliqua*), fennel (*Foeniculum vulgare*), fish poison tree (*Barringtonia asiatica*), garlic (*Allium sativum*), geranium (*Pelargonium hortorum*), juniper (*Juniperus communis*), kava kava (*Piper methysticum*), kopiko ula (*Psychotria hawaiiensis*), lavender (*Lavandula angustifolia*), lemon grass (*Cymbopogon citratus*), mamaki (*Pipturus albidus*), morning glories (*Ipomoea* sp.), mustard seed (*Brassica juncea*), myrtle (*Eugenia umbelliflora*), myrtle (*Pimenta racemosa*), olive (*Olea europaea*), orange (*Citrus sinensis*), oregano (*Origanum vulgare*) palmarosa (*Cymbopogon martini*), patchouli (*Pogostemon cablin*), peppermint (*Mentha piperita*), perilla (*Perilla frutescens*), rose apple bark (*Syzygium jambos*), rose apple, malay (*Eugenia malaccensis*), rosemary (*Rosemarinus officinalis*), shikakai (*Acacia concinna*), tea tree, lemon scented tea tree (*Leptospermum petersonii*), thyme (*Thymus vulgaris*), turpentine (*Pinus palustris*), and combinations thereof.

20. The method of claim 16, wherein the anti-fungal agent is present in an amount from about 0.001% to 10% by weight of the composition.

* * * * *